(12) United States Patent
Grbic et al.

(10) Patent No.: US 9,730,609 B2
(45) Date of Patent: Aug. 15, 2017

(54) METHOD AND SYSTEM FOR AORTIC VALVE CALCIFICATION EVALUATION

(71) Applicants: Sasa Grbic, Erlangen (DE); Razvan Ioan Ionasec, Lawrenceville, NJ (US); Fernando Vega-Higuera, Erlangen (DE); Dominik Bernhardt, Hausen (DE); Dorin Comaniciu, Princeton Junction, NJ (US)

(72) Inventors: Sasa Grbic, Erlangen (DE); Razvan Ioan Ionasec, Lawrenceville, NJ (US); Fernando Vega-Higuera, Erlangen (DE); Dominik Bernhardt, Hausen (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 931 days.

(21) Appl. No.: 13/713,603

(22) Filed: Dec. 13, 2012

(65) Prior Publication Data
US 2013/0155064 A1 Jun. 20, 2013

Related U.S. Application Data

(60) Provisional application No. 61/570,872, filed on Dec. 15, 2011.

(51) Int. Cl.
*A61B 5/055* (2006.01)
*G06T 17/00* (2006.01)
(Continued)

(52) U.S. Cl.
CPC ............... *A61B 5/055* (2013.01); *G06T 7/11* (2017.01); *G06T 7/149* (2017.01); *G06T 7/162* (2017.01);
(Continued)

(58) Field of Classification Search
CPC ......... G06T 7/0012; G06T 2207/30048; A61B 6/032; A61B 6/503; A61B 6/504
(Continued)

(56) References Cited

U.S. PATENT DOCUMENTS 7,803,168 B2    9/2010  Gifford et al.
2003/0176780 A1*  9/2003  Arnold et al. ............... 600/407
(Continued)

OTHER PUBLICATIONS

Razvan Ioan Ionasec et al "Patient-specific modeling and quantification of the aortic and mitral valves from 4-D cardiac CT and TEE", IEEE Transactions on Medical Imaging, vol. 29, pp. 1636-1651, Sep. 2010.*
(Continued)

*Primary Examiner* — Gregory J Tryder
*Assistant Examiner* — Jitesh Patel

(57) ABSTRACT

A method and system for automatic aortic valve calcification evaluation is disclosed. A patient-specific aortic valve model in a 3D medical image volume, such as a 3D computed tomography (CT) volume. Calcifications in a region of the 3D medical image volume defined based on the aortic valve model. A 2D calcification plot is generated that shows locations of the segmented calcifications relative to aortic valve leaflets of the patient-specific aortic valve model. The 2D calcification plot can be used for assessing the suitability of a patient for a Transcatheter Aortic Valve Replacement (TAVI) procedure, as well as risk assessment, positioning of an aortic valve implant, and selection of a type of aortic valve implant.

30 Claims, 4 Drawing Sheets

(51) Int. Cl.
*G06T 7/11* (2017.01)
*G06T 7/149* (2017.01)
*G06T 7/162* (2017.01)

(52) U.S. Cl.
CPC .... *G06T 17/00* (2013.01); *G06T 2207/20081* (2013.01); *G06T 2207/20156* (2013.01); *G06T 2207/30048* (2013.01); *G06T 2207/30101* (2013.01)

(58) Field of Classification Search
USPC .......................................................... 382/131
See application file for complete search history.

(56) References Cited

U.S. PATENT DOCUMENTS

| | | | | |
|---|---|---|---|---|
| 2006/0229303 A1* | 10/2006 | Whitten et al. | ............ | 514/224.5 |
| 2006/0239553 A1* | 10/2006 | Florin et al. | ............ | 382/173 |
| 2007/0211940 A1* | 9/2007 | Fluck et al. | ............ | 382/173 |
| 2008/0279435 A1* | 11/2008 | Arnold et al. | ............ | 382/131 |
| 2009/0123050 A1* | 5/2009 | Ionasec et al. | ............ | 382/131 |
| 2010/0098323 A1* | 4/2010 | Agrawal et al. | ............ | 382/154 |
| 2010/0239148 A1* | 9/2010 | Zheng et al. | ............ | 382/131 |
| 2010/0240996 A1* | 9/2010 | Ionasec et al. | ............ | 600/443 |
| 2011/0257545 A1* | 10/2011 | Suri | ............ | 600/508 |
| 2012/0022843 A1 | 1/2012 | Ionasec et al. | | |
| 2012/0075638 A1* | 3/2012 | Rollins et al. | ............ | 356/479 |
| 2012/0078099 A1* | 3/2012 | Suri | ............ | 600/440 |
| 2012/0243764 A1* | 9/2012 | Dey et al. | ............ | 382/131 |

OTHER PUBLICATIONS

Willmann et al "Electrocardiographically gated multi-detector row CT for assessment of valvular morphology and calcification in Aortic Stenosis", Radiology, vol. 225, Issue 1, pp. 120-128, Oct. 2002.*

Giovanni et al, "Three-dimensional in vivo characterization of calcification in native valves and in Freestyle versus homograft aortic valves", The Journal of Thoracic and Cardiovascular Surgery, vol. 130, No. 1, Jul. 2005.*

Delgado et al, "Automated assessment of the aortic root dimensions with multi-detector row computed tomography", The Annals of Thoracic Surgery; 91, pp. 716-723, Mar. 2011.*

* cited by examiner 400a  400b  400c 600    610    620    630

METHOD AND SYSTEM FOR AORTIC VALVE CALCIFICATION EVALUATION

This application claims the benefit of U.S. Provisional Application No. 61/570,872, filed Dec. 15, 2011, the disclosure of which is herein incorporated by reference.

BACKGROUND OF THE INVENTION

The present invention relates to evaluation of aortic valve calcification, and more particularly, to automated evaluation of aortic valve calcification in medical image data for Transcatheter Aortic Valve Replacement (TAVI) procedures.

In recent years, there has been a major trend in cardiac therapy towards minimally invasive procedures to reduce the risks involved with classical surgical techniques. Percutaneous cardiac interventions, such as TAVI, are becoming the standard therapy for high risk surgical patients. Such procedures off the potential to reduce morbidity, mortality, and costs of surgical valve replacement or repair, while accelerating patient recovery. The TAVI procedure involves accessing a femoral artery, performing balloon valvuloplasty, then advancing an artificial aortic valve across the native valve using a catheter. During rapid right ventricular pacing, a balloon is inflated to deploy the artificial valve. Strokes can be a major complication during TAVI procedures. Magnetic resonance imaging (MRI) studies of cases in which strokes occur, show multifocal areas of cerebral infarction, suggesting embolization. Another drawback of TAVI interventions involves paravalvular leakages, in which blood flows through a channel between the structure of the implanted valve and the cardiac tissue due to a lack of appropriate sealing. Both of these complications are related to calcium deposits inside the aortic valve.

BRIEF SUMMARY OF THE INVENTION

The present invention provides a method and system for automatically evaluating aortic valve calcification in medical image data. Embodiments of the present invention utilize a model based approach to segment the aortic valve and the three aortic leaflets in medical image data, such as 3D computed tomography (CT) data. Embodiments of the present invention detect calcifications within the model and map the calcifications to a 2D plot showing both the location and the severity of the calcifications relative to the aortic valve anatomy. This 2D plot can be used to assess the suitability of a patient for a Transcatheter Aortic Valve Replacement (TAVI) procedure.

In one embodiment, a patient-specific aortic valve model in a 3D medical image volume. Calcifications in a region of the 3D medical image volume defined based on the aortic valve model. A 2D calcification plot is generated that shows locations of the segmented calcifications relative to aortic valve leaflets of the patient-specific aortic valve model.

These and other advantages of the invention will be apparent to those of ordinary skill in the art by reference to the following detailed description and the accompanying drawings.

DETAILED DESCRIPTION

The present invention relates to automatic aortic valve calcification evaluation in medical image data, such as computed tomography (CT) data. Embodiments of the present invention are described herein to give a visual understanding of the aortic valve calcification evaluation method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Recent clinical studies suggest that the amount and distribution of calcifications of the aortic valve have a large influence on the outcome of Transcatheter Aortic Valve Replacement (TAVI) procedures. In particular, the location of the calcified regions relative to the aortic valve leaflets is of high importance. A positive correlation has been shown between post-operative aortic valve regurgitation and the Agatston score calculated from the calcifications in pre-operative CT data. State-of-art CT scanning devices offer good image quality of the aortic valve calcifications, but evaluations are cumbersome for the physician, as the whole process is done manually by first locating the aortic valve and then assessing the 3D region for calcifications manually.

Figure 1:
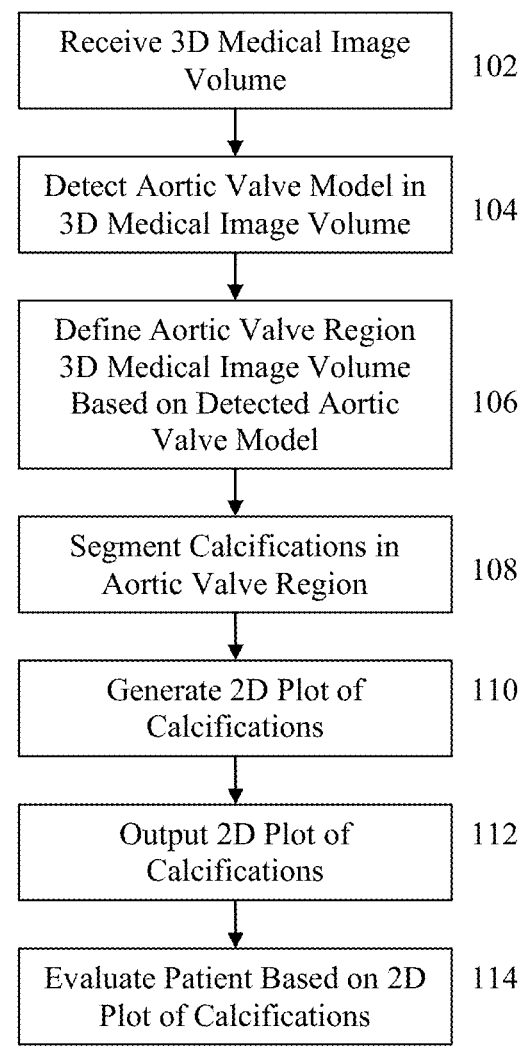
FIG. 1 illustrates a method of automatically evaluating aortic valve calcification in according to an embodiment of the present invention.
Figure 2:
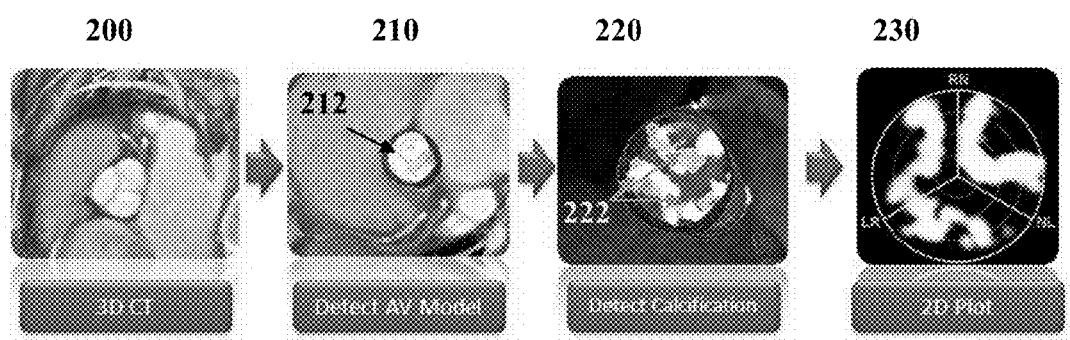
FIG. 2 illustrates exemplary results of the method steps of FIG. 1.

Embodiments of the present invention provide a method and system for automated evaluation of aortic valve calcification. FIG. 1 illustrates a method of automatically evaluating aortic valve calcification in according to an embodiment of the present invention. The method of FIG. 1 transforms medical image data representing the anatomy of a patient's cardiac region into a mapping that shows the location and severity of aortic valve calcifications. FIG. 2 illustrates exemplary results of the method steps of FIG. 1.

Referring to FIG. 1, at step 102, a 3D medical image volume is received. In an advantageous embodiment, the 3D medical image volume is a 3D CT volume of at least a cardiac region of a patient, but the present invention is not limited thereto, and other image modalities, such as magnetic resonance imaging (MRI), ultrasound, etc., may be used as well. The 3D medical image volume may be received directly from an image acquisition device, such as a CT scanner. The 3D medical image volume may also be received by loading a 3D medical image volume that has been stored, for example, in a storage or memory of a computer system. Referring to FIG. 2, image 200 is a view of 3D CT image.

At step 104, a patient-specific aortic valve model is detected in the 3D medical image volume. Image 210 in FIG. 2 shows a patient-specific aortic valve model 212 detected in the 3D CT image 200. In one embodiment, the patient-specific aortic valve model is a physiological model constructed from 11 landmarks (3 commissures, 3 hinges, 3 leaflet tips, and 2 ostias) and four surface structures (aortic root, N-leaflet, L-leaflet, and R-leaflet). The aortic root is constrained by the hinge and the commissure plane, and each leaflet spans between two commissures and one hinge. The patient-specific aortic valve model can be extracted in the 3D medical image volume by estimating a mean shape model of the aortic valve learned from a set of training data in the image using machine learning techniques. In particular, the patient-specific parameters of the physiological aortic valve model can be estimated from the 3D medical image volume using a hierarchical approach within a Marginal Space Learning (MSL) framework. Additional details regarding hierarchical approaches for detecting a patient-specific aortic valve model are described in United States Published Patent Application No. 2012/0022843, entitled "Method and System for Comprehensive Patient-Specific Modeling of the Heart" and United States Published Patent Application No. 2009/0123050, entitled "Method and System for Automatic Quantification of Aortic Valve Function from 4D Computed Tomography Data Using a Physiological Model", the disclosures of which are incorporated herein by reference.

The idea of MSL is not to learn a classifier directly in the full similarity transformation space, but to incrementally learn classifiers in the series of marginal spaces with increasing dimensionality. As the dimensionality increases, the valid space region becomes more restricted by previous marginal space classifiers. In one embodiment, separate detectors are successively trained based on annotated training data using a Probabilistic Boosting Tree (PBT) with Haar features and Steerable features, and consequently applied to estimate rigid motion parameters, followed by the anatomical landmarks of the aortic valve model, and then the surface structures of the aortic valve model.

Figure 3:
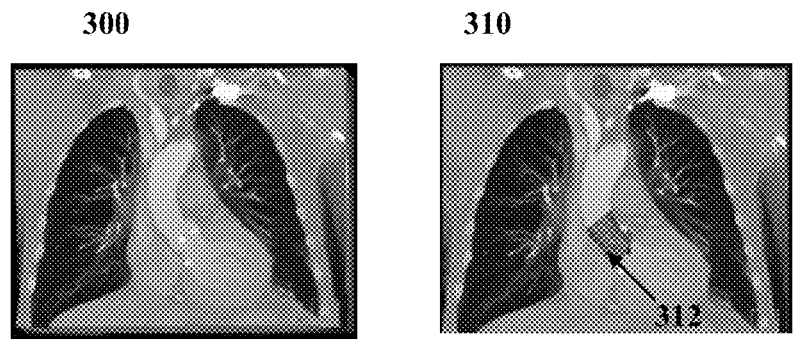
FIG. 3 illustrates exemplary patient-specific aortic valve detection results.
Figure 4:
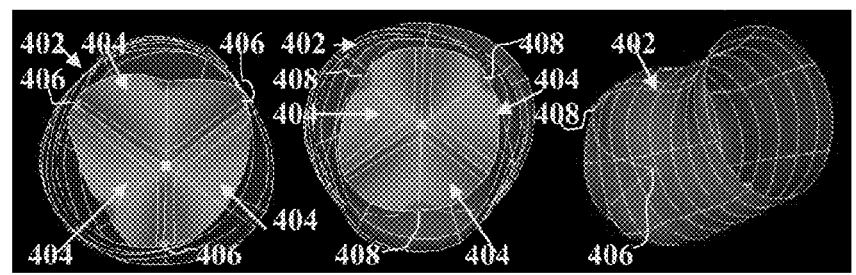
FIG. 4 illustrates a detailed view of a patient-specific aortic valve model estimated from a 3D CT image.

FIG. 3 illustrates exemplary patient-specific aortic valve detection results. As illustrated in FIG. 3, image 300 shows a volumetric CT image of a patient's thorax and image 310 shows a patient-specific aortic valve model 312 detected in the volumetric CT image. FIG. 4 illustrates a detailed view of a patient-specific aortic valve model estimated from a 3D CT image. In particular, FIG. 4 shows a top view 400a, bottom view 400b, and side view 400c of a patient-specific aortic valve model including the aortic root 402, aortic valve leaflets 404, aortic valve commissures 406, and aortic valve hinges 408.

Returning to FIG. 1, at step 106, a region of the 3D medical image volume is defined based on the detected patient-specific aortic valve model. In particular, the volumetric region defined by the boundaries of the detected aortic valve model can be cropped in order to define a region of interest in the 3D medical image volume for segmenting calcified regions.

At step 108, calcifications are segmented in the defined region of the 3D medical image volume. In an advantageous embodiment, graph cuts segmentation can be used to segment the calcifications. In this case, each voxel in the defined region can be classified using a trained calcification detector that has been trained based on annotated training data. The voxel having the highest classification probability is used as the positive seed point and the voxel having the lowest classification probability is used as the negative seed point. A graph cuts segmentation algorithm segment the calcifications. In graph cuts segmentation, each voxel is represented as a vertex in an undirected graph, with edges connecting the vertices. An optimal cut is determined to cut the edges of the graph so that each vertex is connected to either the positive seed point or the negative seed point. The vertices connected to the positive seed point represent calcification voxels. The classification probabilities of the voxels determined by the trained calcification detector can be used as node weights for the graph cuts segmentation.

Image 220 of FIG. 2 shows calcifications 222 segmented in the region defined by the aortic valve model 212 using graph cuts segmentation. Although in the embodiment described above, graph cuts segmentation is used to segment the calcifications, the present invention is not limited thereto. It is also possible that other segmentations techniques, such as a random walker segmentation algorithm, intensity-based thresholding, or machine-learning based classification can be used to implement the calcification segmentation.

At step 110, a 2D plot of the calcifications is generated. Image 230 of FIG. 2 illustrates a 2D calcification plot generated based on the segmented calcifications 222. The 2D plot of the calcifications is generated by mapping each segmented calcification region to one of the three aortic valve leaflets on the detected patient-specific aortic valve model. Each segmented calcification voxel is mapped to a closest mesh point on one of the three aortic valve leaflets in the detected aortic valve model. The 2D calcification plot is a circle and each leaflet is represented as one third of the circle in the 2D calcification plot. Accordingly, each leaflet mesh point has a fixed correspondence with one point on the 2D calcification plot. Each mesh point of the aortic valve model can be represented with the coordinates (u,v), where u and v are circumferential and longitudinal directions, respectively. All of the segmented calcification voxels are mapped to the nearest leaflet mesh point, and the leaflet mesh points are then projected onto a 2D circular plane such that points having the same u coordinate value and different v coordinate values are projected to the same point on the 2D plot. Thus, the amount of calcification at each point on the 2D plot is a result of calcifications being accumulated in the longitudinal direction over the entire aortic root. The amount of calcification can be encoded with the alpha channel, which controls the level of transparency. Accordingly, small amounts of calcification will appear transparent, while severe calcifications will appear solid in the 2D plot. Accordingly, the 2D plot shows both the location of the segmented calcifications with respect to the aortic valve leaflets and the severity of the calcifications.

Figure 5:
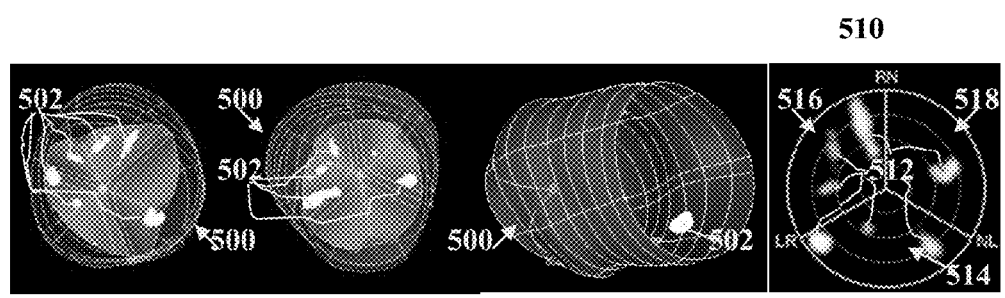
FIG. 5 illustrates generation of a 2D calcification plot.

FIG. 5 illustrates generation of a 2D calcification plot. In particular, FIG. 5 shows top, bottom, and side views of a patient-specific aortic valve model 500, calcifications 502 detected in the volumetric region of a 3D CT image defined by the aortic valve model 500, and a 2D calcification plot 510 generated from the segmented calcifications 502. The 2D calcification plot 510 shows the positions of calcifications 512 relative to the L-leaflet 514, R-leaflet 516, and N-leaflet 518. The level of transparency of the calcifications 512 in the 2D calcification plot 510 also shows the relative severity of the calcifications 512.

Figure 6:
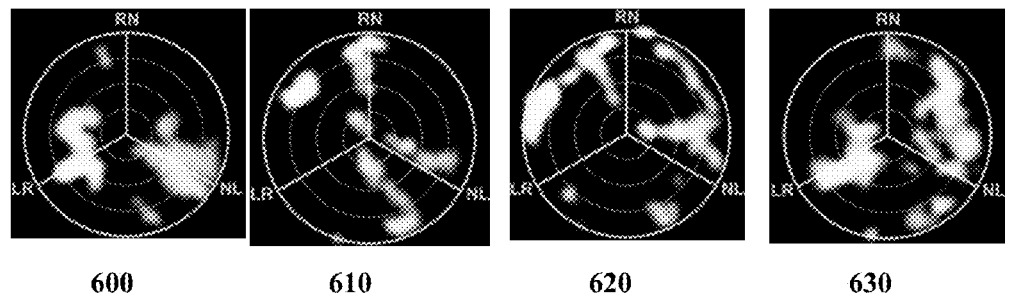
FIG. 6 illustrates exemplary 2D calcification plots generated using the method of FIG. 1.

Returning to FIG. 1, at step 112, the 2D plot of 2D calcifications is output. For example, the 2D calcification plot can be output by displaying the 2D calcification plot on a display of a computer device or printing an image of the 2D calcification plot. The 2D calcification plot can also be output by storing the 2D calcification plot, for example in a storage or memory of a computer system. FIG. 6 illustrates exemplary 2D calcification plots generated using the method of FIG. 1. As shown in FIG. 6, calcification plots 600, 610, 620, and 630 were generated from different 3D CT datasets.

At step 114, the patient is evaluated based on the 2D calcification plot. The mapping of the calcifications to the 2D plot enables comprehensive calcium analysis across patient populations in a comparable way. Accordingly, calcium distribution patterns can be correlated to outcomes of TAVI procedures. In one embodiment, a 2D calcification plot generated using pre-operative CT data for a patient can be used to automatically determine whether the patient is suitable for a TAVI procedure. In this case, a database of 2D calcification plots as known results of TAVI procedures can be used to train a classifier using machine learning techniques. The trained classifier can then automatically determine whether a patient is suitable for a TAVI procedure based on the 2D calcification plot generated for the patient. Similarly, such a technique can be used for risk assessment, such as to predict the likelihood that a TAVI procedure will result in the patient having a stroke. In addition, the information about the locations and severity of the calcifications can be used to define the best positioning of an aortic valve implant. The type of implant device can also be automatically selected based on an evaluation of the 2D calcification plot generated for a patient.

Figure 7:
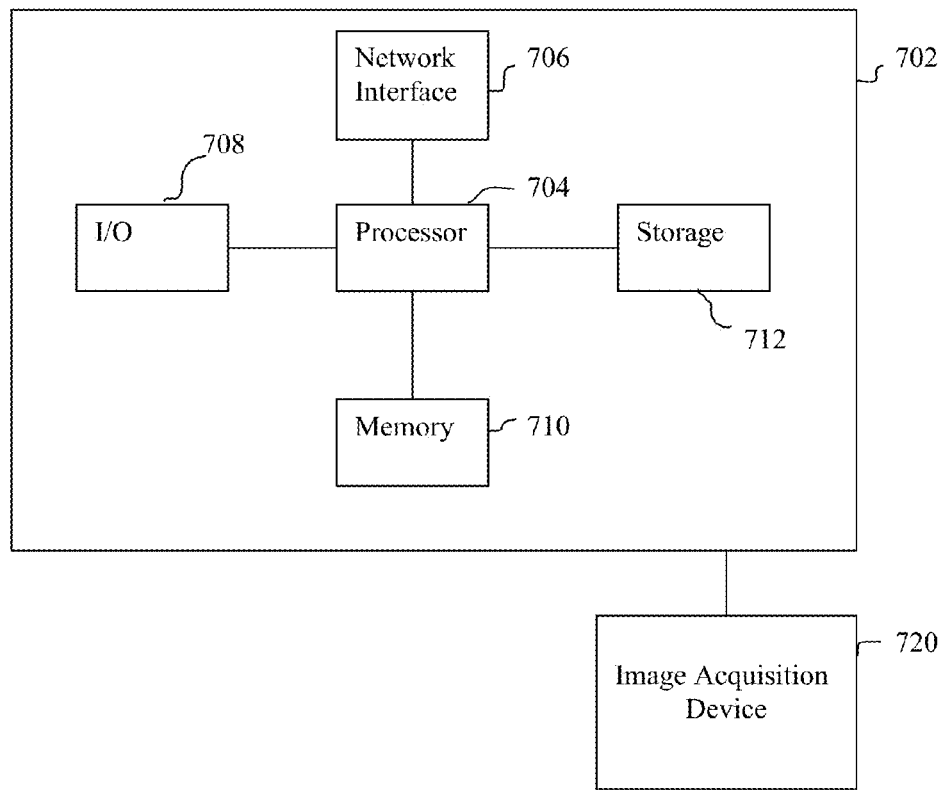
FIG. 7 is a high-level block diagram of a computer capable of implementing the present invention.

The above-described methods for automated aortic valve calcification evaluation may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the method of FIG. 1 may be defined by the computer program instructions stored in the memory 710 and/or storage 712 and controlled by the processor 704 executing the computer program instructions. An image acquisition device 720, such as a CT scanner, can be connected to the computer 702 to input image data to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). Such input/output devices 708 may be used in conjunction with a set of computer programs as an annotation tool to annotate volumes received from the image acquisition device 720. One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automatic aortic valve calcification evaluation, comprising:
   detecting a patient-specific aortic valve model in a 3D medical image volume;
   segmenting calcifications in a region of the 3D medical image volume defined based on the aortic valve model; and
   generating a 2D calcification plot showing locations of the segmented calcifications relative to aortic valve leaflets of the patient-specific aortic valve model.

2. The method of claim 1, wherein detecting a patient-specific aortic valve model in a 3D medical image volume comprises:
   detecting the patient-specific aortic valve model in the 3D medical volume using a Marginal Space Learning (MSL) framework.

3. The method of claim 1, wherein detecting a patient-specific aortic valve model in a 3D medical image volume comprises:
   detecting rigid motion parameters in the 3D medical image volume using a first trained detector;
   detecting anatomical landmarks in the 3D medical image volume based on the detected rigid motion parameters using a second trained detector; and
   detecting surface aortic valve surface structures in the 3D medical image volume based on the detected anatomical landmarks using a third trained detector.

4. The method of claim 3, wherein the anatomical landmarks include aortic valve hinges and aortic valve commissures and the aortic valve surface structures include an aortic root and the aortic valve leaflets.

5. The method of claim 1, wherein segmenting calcifications in a region of the 3D medical image volume defined based on the aortic valve model comprises:
   segmenting the calcifications in the region of the 3D medical image volume using graph cuts segmentation.

6. The method of claim 5, wherein segmenting the calcifications in the region of the 3D medical image volume using graph cuts segmentation comprises:
   determining a probability score for each of a plurality of voxels in the region of the 3D medical image using a trained calcification detector;
   assigning a voxel having a highest probability score as a positive seed point and a voxel having a lowest probability score as a negative seed point; and
   segmenting a set of calcification voxels from the plurality of voxels using graph cuts segmentation based on the positive seed point, the negative seed point, and the probability scores for the plurality of voxels.

7. The method of claim 1, wherein segmenting calcifications in a region of the 3D medical image volume defined based on the aortic valve model comprises:
   detecting a set of calcification voxels from a plurality of voxels in the region of the 3D medical image volume.

8. The method of claim 1, wherein generating a 2D calcification plot showing locations of the segmented calcifications relative to aortic valve leaflets of the patient-specific aortic valve model comprises:
   mapping the segmented calcifications closest mesh points on the aortic valve leaflets of the patient-specific aortic valve model; and
   projecting the calcifications mapped to each of the mesh points on the aortic valve leaflets of the patient-specific aortic valve model to a corresponding point on a circular 2D plot, wherein each aortic valve leaflet is represented as one third of the circular 2D plot.

9. The method of claim 1, wherein the 2D calcification plot shows relative severity of the calcifications using relative levels of transparency.

10. The method of claim 1, further comprising:
determining a patient's suitability for a Transcatheter Aortic Valve Replacement (TAVI) procedure based on the 2D calcification plot using a trained classifier.

11. The method of claim 1, further comprising:
determining a risk of stroke for a patient based on the 2D calcification plot using a trained classifier.

12. The method of claim 1, further comprising:
determining a best position for an aortic valve implant based on the 2D calcification plot.

13. The method of claim 1, further comprising:
automatically selecting a type of aortic valve implant device based on the 2D calcification plot.

14. An apparatus for automatic aortic valve calcification evaluation, comprising:
means for detecting a patient-specific aortic valve model in a 3D medical image volume;
means for segmenting calcifications in a region of the 3D medical image volume defined based on the aortic valve model; and
means for generating a 2D calcification plot showing locations of the segmented calcifications relative to aortic valve leaflets of the patient-specific aortic valve model.

15. The apparatus of claim 14, wherein the patient-specific aortic valve model comprises an aortic root surface model and aortic valve leaflet surface models.

16. The apparatus of claim 14, wherein the means for segmenting calcifications in a region of the 3D medical image volume defined based on the aortic valve model comprises:
means for segmenting the calcifications in the region of the 3D medical image volume using graph cuts segmentation.

17. The apparatus of claim 14, wherein the means for segmenting calcifications in a region of the 3D medical image volume defined based on the aortic valve model comprises:
means for detecting a set of calcification voxels from a plurality of voxels in the region of the 3D medical image volume.

18. The apparatus of claim 14, wherein the means for generating a 2D calcification plot showing locations of the segmented calcifications relative to aortic valve leaflets of the patient-specific aortic valve model comprises:
means for mapping the segmented calcifications closest mesh points on the aortic valve leaflets of the patient-specific aortic valve model; and
means for projecting the calcifications mapped to each of the mesh points on the aortic valve leaflets of the patient-specific aortic valve model to a corresponding point on a circular 2D plot, wherein each aortic valve leaflet is represented as one third of the circular 2D plot.

19. The apparatus of claim 14, wherein the 2D calcification plot shows relative severity of the calcifications using relative levels of transparency.

20. A non-transitory computer readable medium storing computer program instructions for automatic aortic valve calcification evaluation, the computer program instructions when executed on a processor cause the processor to perform operations comprising:
detecting a patient-specific aortic valve model in a 3D medical image volume;
segmenting calcifications in a region of the 3D medical image volume defined based on the aortic valve model; and
generating a 2D calcification plot showing locations of the segmented calcifications relative to aortic valve leaflets of the patient-specific aortic valve model.

21. The non-transitory computer readable medium of claim 20, wherein detecting a patient-specific aortic valve model in a 3D medical image volume comprises:
detecting rigid motion parameters in the 3D medical image volume using a first trained detector;
detecting anatomical landmarks in the 3D medical image volume based on the detected rigid motion parameters using a second trained detector; and
detecting surface aortic valve surface structures in the 3D medical image volume based on the detected anatomical landmarks using a third trained detector.

22. The non-transitory computer readable medium of claim 21, wherein the anatomical landmarks include aortic valve hinges and aortic valve commissures and the aortic valve surface structures include an aortic root and the aortic valve leaflets.

23. The non-transitory computer readable medium of claim 20, wherein segmenting calcifications in a region of the 3D medical image volume defined based on the aortic valve model comprises:
segmenting the calcifications in the region of the 3D medical image volume using graph cuts segmentation.

24. The non-transitory computer readable medium of claim 23, wherein segmenting the calcifications in the region of the 3D medical image volume using graph cuts segmentation comprises:
determining a probability score for each of a plurality of voxels in the region of the 3D medical image using a trained calcification detector;
assigning a voxel having a highest probability score as a positive seed point and a voxel having a lowest probability score as a negative seed point; and
segmenting a set of calcification voxels from the plurality of voxels using graph cuts segmentation based on the positive seed point, the negative seed point, and the probability scores for the plurality of voxels.

25. The non-transitory computer readable medium of claim 20, wherein generating a 2D calcification plot showing locations of the segmented calcifications relative to aortic valve leaflets of the patient-specific aortic valve model comprises:
mapping the segmented calcifications closest mesh points on the aortic valve leaflets of the patient-specific aortic valve model; and
projecting the calcifications mapped to each of the mesh points on the aortic valve leaflets of the patient-specific aortic valve model to a corresponding point on a circular 2D plot, wherein each aortic valve leaflet is represented as one third of the circular 2D plot.

26. The non-transitory computer readable medium of claim 25, wherein the 2D calcification plot shows relative severity of the calcifications using relative levels of transparency.

27. The non-transitory computer readable medium of claim 20, wherein the operations further comprise:
determining a patient's suitability for a Transcatheter Aortic Valve Replacement (TAVI) procedure based on the 2D calcification plot using a trained classifier.

28. The non-transitory computer readable medium of claim 20, wherein the operations further comprise:

determining a risk of stroke for a patient based on the 2D calcification plot using a trained classifier.

29. The non-transitory computer readable medium of claim 20, wherein the operations further comprise:
determining a best position for an aortic valve implant based on the 2D calcification plot.

30. The non-transitory computer readable medium of claim 20, wherein the operations further comprise:
automatically selecting a type of aortic valve implant device based on the 2D calcification plot.

* * * * *